US008465423B2

(12) United States Patent
Hasbun

(10) Patent No.: US 8,465,423 B2
(45) Date of Patent: Jun. 18, 2013

(54) PORTABLE DIAGNOSTIC INSTRUMENT AND A METHOD FOR ITS USE

(76) Inventor: William M. Hasbun, Mount Laurel, NJ (US)

(*) Notice: Subject to any disclaimer, the term of this patent is extended or adjusted under 35 U.S.C. 154(b) by 683 days.

(21) Appl. No.: 12/606,996

(22) Filed: Oct. 27, 2009

(65) Prior Publication Data
US 2010/0105988 A1 Apr. 29, 2010

Related U.S. Application Data

(60) Provisional application No. 61/108,564, filed on Oct. 27, 2008.

(51) Int. Cl.
A61B 1/32 (2006.01)

(52) U.S. Cl.
USPC ............................................ 600/235; 600/200

(58) Field of Classification Search
USPC .................. 600/202, 240, 241, 245, 246, 200, 600/235, 197
See application file for complete search history.

(56) References Cited

U.S. PATENT DOCUMENTS

| 3,760,798 | A |   | 9/1973  | Edinger              |
|-----------|---|---|---------|----------------------|
| 3,812,847 | A | * | 5/1974  | Moore et al. 600/200 |
| 3,978,850 | A |   | 9/1976  | Moore et al.         |
| 4,147,163 | A |   | 4/1979  | Newman et al.        |
| 5,429,119 | A |   | 7/1995  | Griffin et al.       |
| 6,152,873 | A |   | 11/2000 | Rogers               |
| 6,383,133 | B1 |  | 5/2002  | Jones                |
| 6,393,431 | B1 |  | 5/2002  | Salvati et al.       |
| 7,029,439 | B2 |  | 4/2006  | Roberts et al.       |
| 7,137,948 | B2 |  | 11/2006 | Tsai                 |
| 7,160,013 | B2 |  | 1/2007  | Kirchner             |
| 2005/0143626 | A1 | | 6/2005  | Prescott             |

* cited by examiner

Primary Examiner — Andrew Yang
(74) Attorney, Agent, or Firm — Muskin & Cusick, LLC; Shawn R. Farmer; Jon H. Muskin

(57) ABSTRACT

A portable diagnostic instrument for use by medical professionals. The portable diagnostic instrument can comprise a circuit control that can maintain the output of the light intensity constant, even when battery power is reduced. The circuit control system can also comprise a warning system to provide information about remaining battery life to the user. Furthermore, the portable diagnostic instrument can comprise an otoscope further comprising a separate, folding magnifying lens assembly and a separate, folding specula assembly.

14 Claims, 5 Drawing Sheets

PORTABLE DIAGNOSTIC INSTRUMENT AND A METHOD FOR ITS USE

CROSS REFERENCE TO RELATED APPLICATIONS

This application claims benefit to provisional application no. 61/108,564 filed Oct. 27, 2008, which is incorporated by reference herein in its entirety.

FIELD OF THE INVENTION

This device relates to compact and illuminated diagnostic equipment for use by medical professionals. More particularly it relates to a portable diagnostic instrument that is capable of folding into a protective casing allowing for easy carrying and protection from impact and environmental threats. Each portable diagnostic instrument is provided illumination through the use of one or more photodiodes from which the light intensity will not instantly decrease as the battery power is reduced. This allows the device to be useful until the batteries have been almost fully discharged.

BACKGROUND

Portable medical diagnostic equipment can be carried by a doctor or by other medical personnel to provide quick access when examining a patient. Additionally, such devices are generally kept in a pocket, so that they do not get misplaced and are available whenever needed. These devices must be capable of accepting disposable specula covers or other disposable pieces, so that they can be used on different patients without spreading germs. These devices must also be able to provide illumination of the part of the patient being examined and must be reliable. It is an advantage of these devices to be capable of providing more than one function, such as that of an otoscope and a flashlight. Therefore, it is beneficial if such devices can be capable of housing many different diagnostic tools in one piece of equipment, which can be easily transported and readily accessible to medical professionals. It can also be beneficial if such devices contain a power source and one or more self-contained illumination sources, which can provide a sufficient amount of light to effectively illuminate the part of the patient being examined. Additionally, it is beneficial if such devices can provide an indicator informing the user when power is getting low, before the device ceases to operate correctly.

A related invention, Moore U.S. Pat. No. 3,812,847, describes a "Combination battery handle-case for a pair of attached, outfolding illuminated medical instruments." As with the present device, the Moore invention describes a portable diagnostic device that has different illuminated medical instruments that can be folded into a closed position within the case, and folded out of the case and into a usable position. However, the Moore invention, while capable of providing illumination to the instruments, does not control the intensity of the light, or attempt to extend the useful battery life in any way. Additionally, this device does not provide any warning that the battery power is getting low or that the illuminating features of the instruments will be useless in the near future. Furthermore, the Moore invention can only hold two diagnostic tools, one at each end of the case.

Another related invention, Griffin U.S. Pat. No. 5,429,119, existing in the prior art, describes a "hand-held compact diagnostic device." The Griffin patent describes a diagnostic device for use in the medical profession, which provides a portable case containing multiple different medical instruments. The Griffin invention provides a stem to which multiple different instrument heads can be attached, illuminated and folded into the case. However, the Griffin patent does not describe any circuit feature that controls the output intensity of the light in relation to the battery power. Additionally, the Griffin patent does not describe medical instruments that do not require being screwed onto a stem.

What is needed is a portable diagnostic instrument comprising a circuit control that maintains the output of the light intensity constant, even when battery power is reduced. Additionally, a warning system is needed to provide information about the remaining battery life to the user. Furthermore, a portable diagnostic device is needed that comprises an otoscope further comprising one or more photodiodes in its specula providing a light source. Moreover, a device is needed that can house diagnostic instruments that do not require being attached to the device through the use of a hinge or screw system along with those that are attached through the use of a hinge.

SUMMARY OF THE INVENTION

It is an aspect of the present device to provide an improved portable diagnostic instrument.

The above aspect can be obtained by a portable diagnostic instrument comprising a case capable of housing the components of the portable diagnostic instrument; a specula assembly and a magnifying lens assembly capable of being used together to form an otoscope, wherein each can unfold from the case separately and the specula assembly contains a light source; processors and sensors capable of measuring the amount of electricity provided to the light source by a battery and increasing amperage from the battery in order provide constant light output until the battery can no longer provide voltage or amperage sufficient to maintain the constant light output; and a warning system comprising sensors and processors, which can determine when the battery is about to fail and notify the user of the portable diagnostic instrument.

BRIEF DESCRIPTION OF THE DRAWINGS

Further features and advantages of the present device, as well as the structure and operation of various embodiments of the present device, will become apparent and more readily appreciated from the following description of the preferred embodiments, taken in conjunction with the accompanying drawings of which.

DETAILED DESCRIPTION

Figure 1:
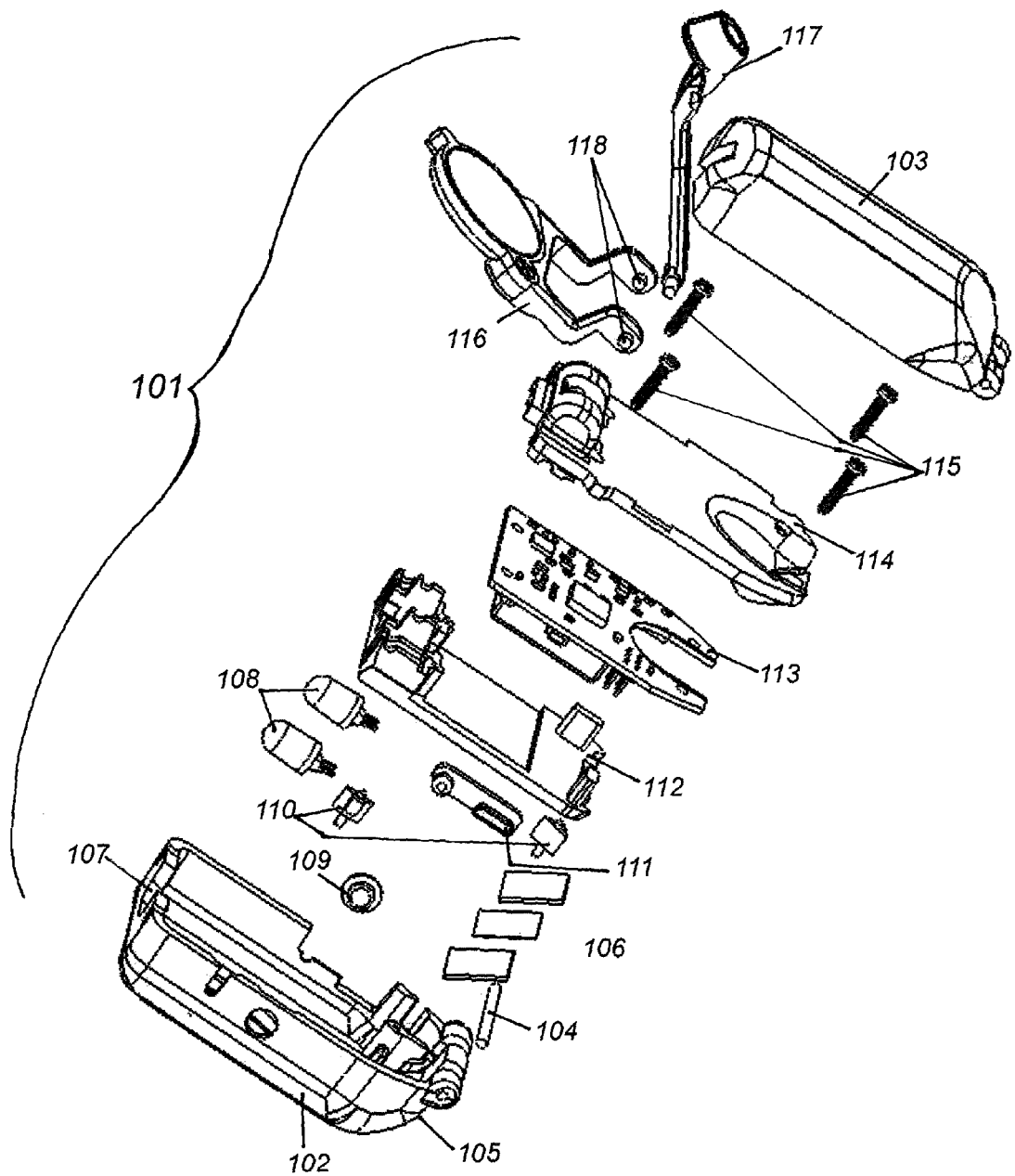
FIG. 1 is an exploded view of a portable diagnostic instrument according to an embodiment.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Reference will now be made in detail to the presently preferred embodiments of the invention, examples of which are illustrated in the accompanying drawings, wherein like reference numerals refer to like elements throughout.

FIG. 1 is an exploded view of a portable diagnostic instrument 101 according to an embodiment.

Referring to FIG. 1, the entire portable diagnostic instrument 101 can be contained within the housing bottom 102 and the housing cover 103, which can be held together though the use of a hinge pin 104 that connects the two pieces together such that the housing cover 103 and housing bottom 102 can rotate relative to each other about a hinged joint created by the hinge pin 104. This movement can allow the housing cover 103 and the housing bottom 102 to be in a closed position to protect the instruments inside the device 101 or in an opened position to allow access to the instruments inside the device 101.

The housing bottom 102 can comprise an opening 105 under the hinge in which a blue film 106 can be inserted for use in observing damage to an eye, which is visible after the introduction of fluorescein dye into the eye. The opposite end of the housing bottom 102 can comprise another opening 107, in which one or more light emitting diodes 108 can be located to provide a light source for examining a patient. The housing bottom 102 can also comprise a switch cap 109, clear plastic light pipes 110 made of a fiber optic material and a gasket 111 to cover a charger port (not pictured). These pieces can all be held in place through the use of the housing bottom floor 112, which can be located inside the housing bottom 102 and can provide a mount for the other pieces that can be located inside the device 101. The housing bottom 102 can be comprised of plastic, metal, wood or any other material or combination of suitable material known to one of ordinary skill in the art.

Located adjacent to the housing bottom floor 112 can be a circuit board 113 and batteries (not shown). These batteries can be rechargeable and can supply power to illumination sources 108 and 204 and indicator lights for both battery life and charging status (not shown). The circuit board 113 can comprise sensors and processors which can maintain a constant intensity of the light, even if the batteries' potential begins to diminish by increasing the electrical current. The circuit board 113 can be protected and held in place by a circuit board cover 114, which can be attached to the circuit board 113, the housing bottom floor 112 and the housing bottom 102 through the use of screws 115 or any other suitable fastener known to one of ordinary skill in the art.

Finally, the magnifying lens assembly 116 and the specula assembly 117 can be connected to the circuit board cover 114 through the use of pegs 118 that can be inserted into receptor holes (not shown) that allow the magnifying lens assembly 116 and the specula assembly 117 to rotate freely about the hinge from inside of the portable diagnostic instrument 101 to its outside, where both sections 116 and 117 can be used in conjunction to create a functioning otoscope.

Figure 2:
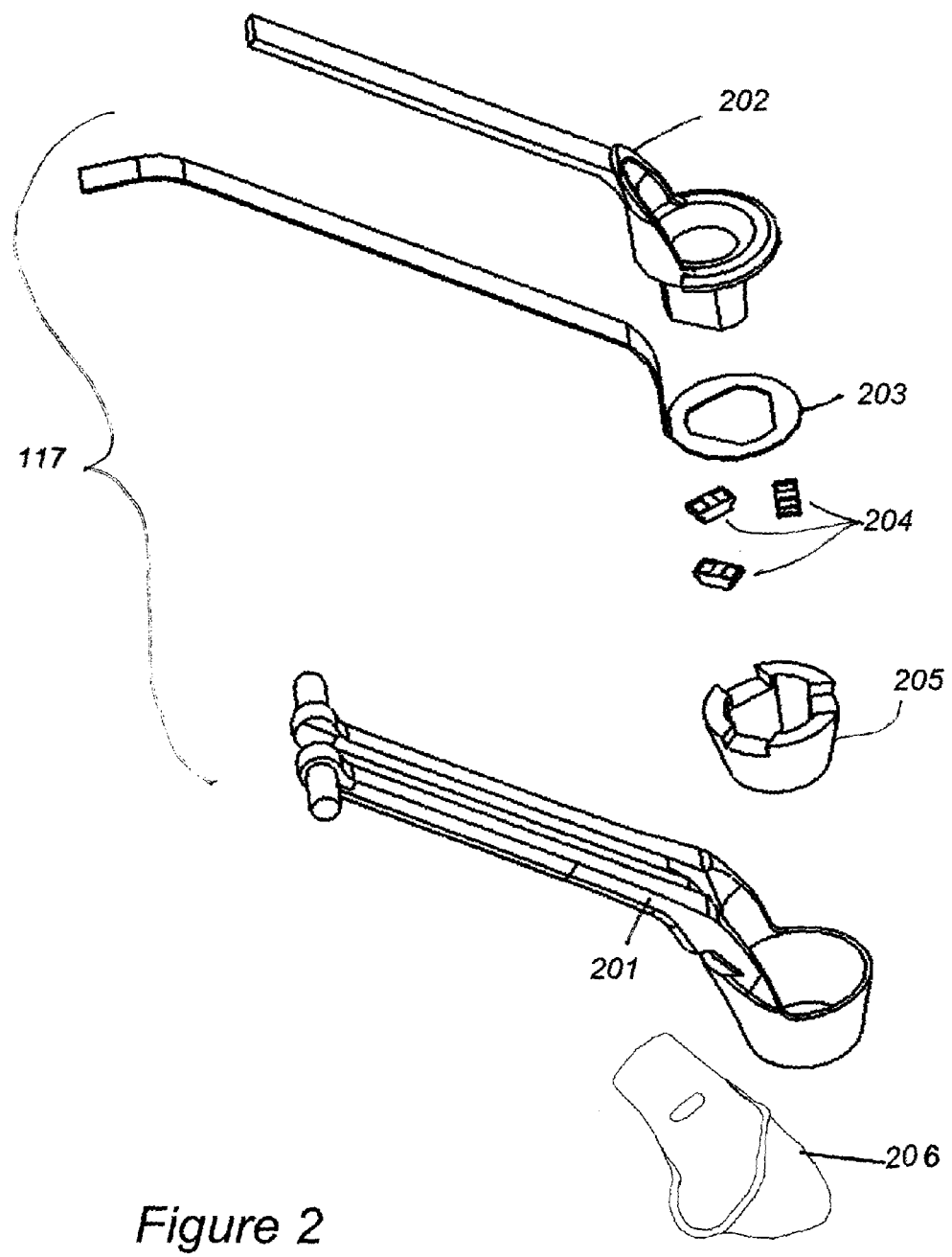
FIG. 2 is an exploded view of a specula assembly of a portable diagnostic instrument according to an embodiment.

FIG. 2 is an exploded view of a specula assembly 117 of a portable diagnostic instrument 101 according to an embodiment.

The specula assembly 117 can comprise a specula housing 201 and a molded plastic cover 202 which can hold the pieces of the specula assembly 117 in place. The specula housing 201 can be made of plastic, metal or other suitable material and can connect to the circuit board cover 114 to form a hinge movement. The specula housing 201 can have a conical shape for holding the ear open, while being examined. The specula housing 201 can also receive a disposable specula cover 206 that can fit over the specula housing 201, which would make contact with the patient. By disposing of the specula cover 206 after examining each patient, the specula assembly 117 can remain sanitary.

The specula assembly 117 can comprise a flexible printed circuit board 203, which can provide power to surface mount photodiodes 204. The printed flexible circuit board 203 can also provide control of the power supplied to the surface mount photodiodes 204. The surface mount photodiodes 204 provide illumination to the specula assembly 117 when it is in use as an otoscope. Light from the surface photodiodes 204 can pass through a clear acrylic light pipe 205 and travel through the specula housing 201 to be focused onto the subject being observed. In an alternative embodiment, a hollow, conical photodiode can be used in place of the surface mount photodiodes 204 and the clear acrylic light pipe 205.

Figure 3:
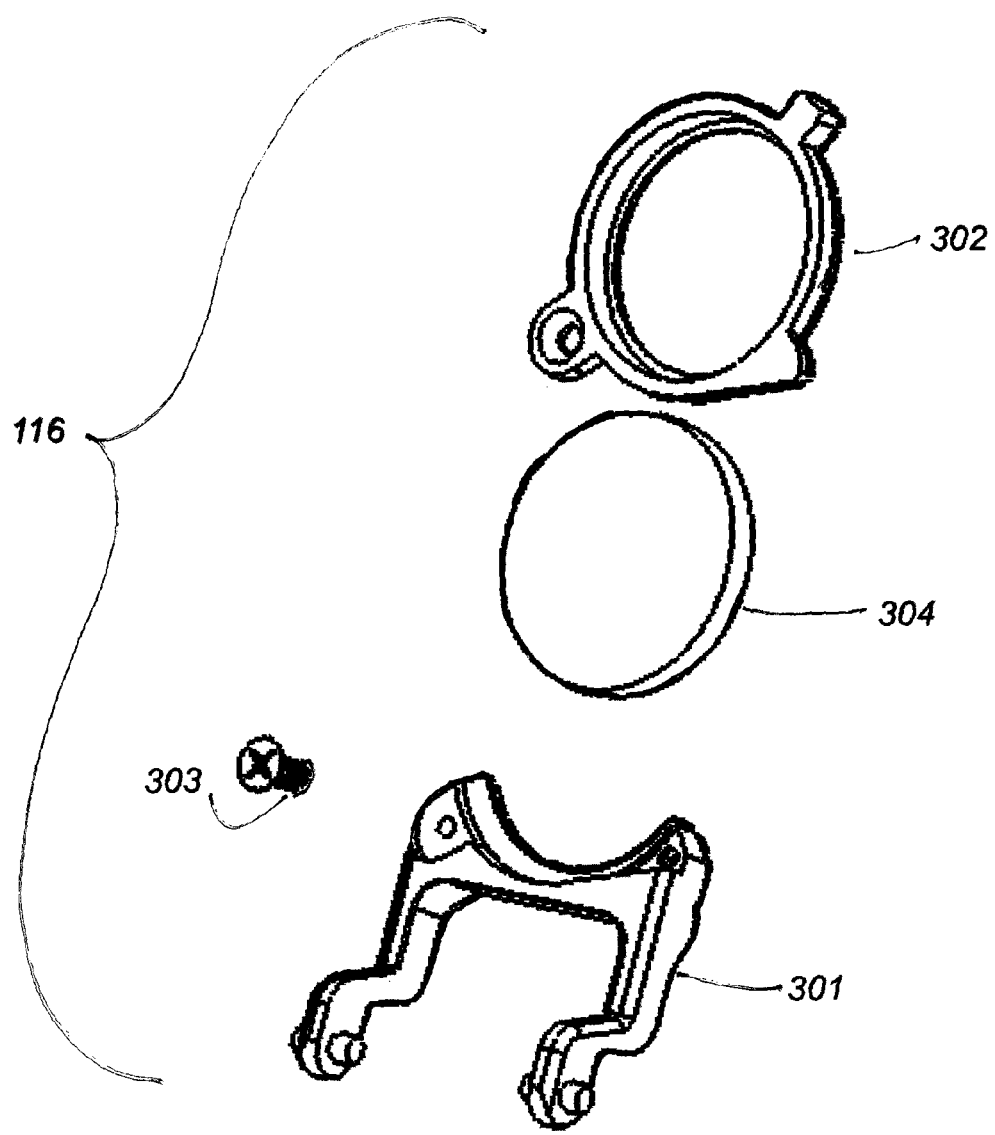
FIG. 3 is an exploded view of a magnifying lens assembly of a portable diagnostic instrument according to an embodiment.

FIG. 3 is an exploded view of a magnifying lens assembly 116 of a portable diagnostic instrument 101 according to an embodiment.

The magnifying lens assembly 116 can comprise four pieces, as shown in FIG. 3. A support piece 301 can connect the assembly 116 to a circuit board cover 114 using pegs 118 to form a hinge. The support piece also has a lens holder 302, which can be rotatably connected to the end of the support piece 301 through the use of a screw 303 or other suitable connecting fastener. The screw attachment allows the lens holder 302 to pivot radially about the assembly 116. This movement allows the user access to the specula assembly 117 or the specimen that is being examined allowing the user to remove an object from the ear. The lens holder 302 can hold a magnifying lens 304 made of a hard plastic material or any other material suitable for a magnifying lens.

Figure 4:
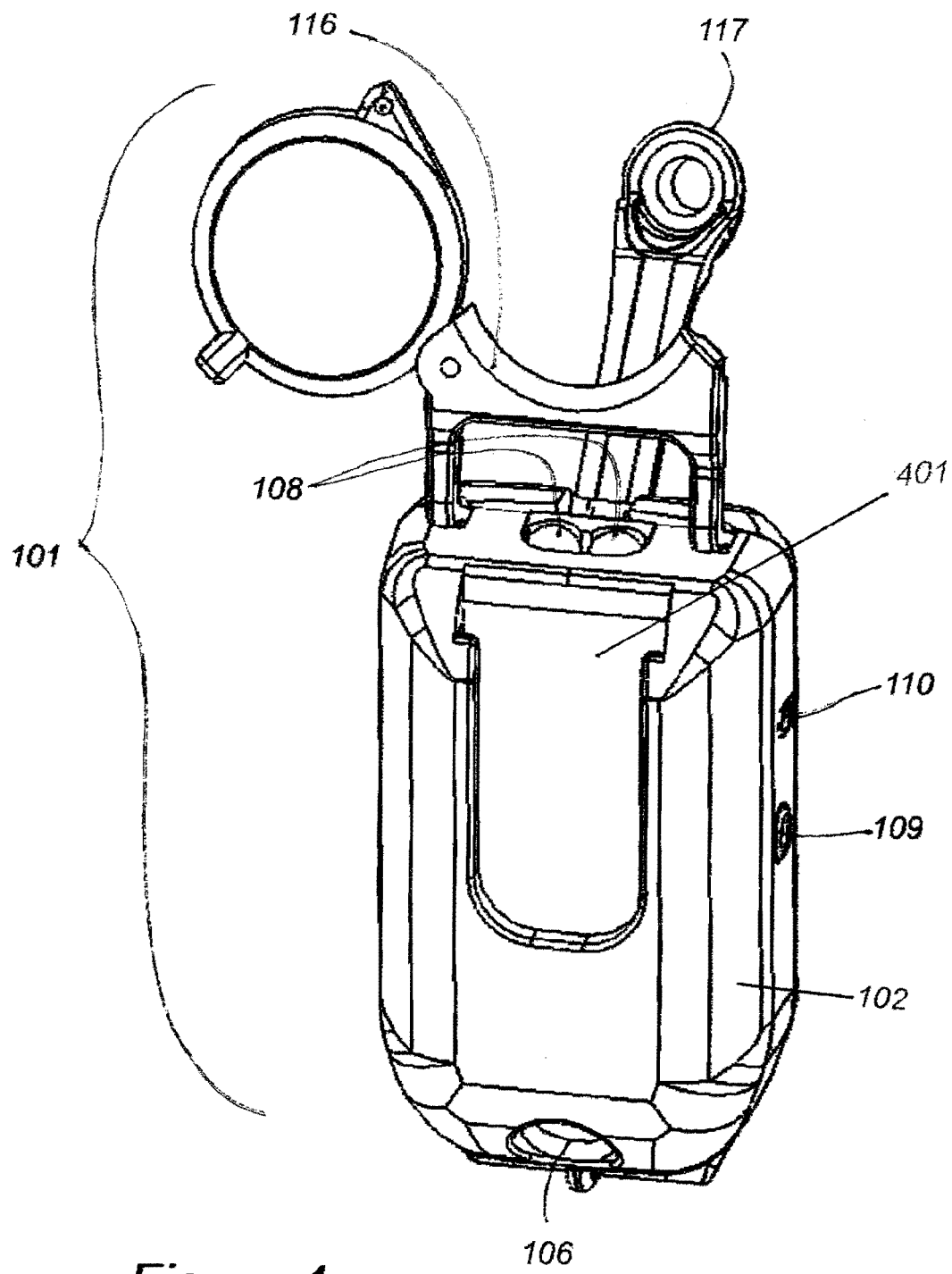
FIG. 4 is a view of a portable diagnostic instrument with its cover in a closed position and its magnifying lens assembly and specula assembly in the open, usable position creating an otoscope according to an embodiment.

FIG. 4 is a view of a portable diagnostic instrument 101 with its cover 103 in a closed position and its magnifying lens assembly 116 and specula assembly 117 in the open, usable position creating an otoscope according to an embodiment.

FIG. 4 demonstrates an otoscope configuration using the magnifying lens assembly 116 and specula assembly 117 of a portable diagnostic instrument 101 to create an otoscope. Both of the assemblies 116 and 117 can be extended in their open positions and the housing cover 103 can be in its closed position. This configuration allows for easy handling of the magnifying lens assembly 116 and specula assembly 117 and protection of the circuitry and instruments contained within the device 101.

A power switch 109 can be used to control the illumination sources including the light emitted diodes 108 and the surface mount photodiodes 203 within the otoscope assembly 117. Above the power switch 109 can be a clear plastic light pipe 110, with a light emitting diode (not shown) of more than one color located to the inside of the light pipe 110. The light emitting diode can be part of a warning unit which can provide an indication of the battery level. The diode can be one color when fully charged and another when a charge is needed soon and can flash when the device should not be used and needs to be recharged.

The housing bottom 102 can comprise a slot 401 which can receive a standard tongue depressor. The slot 401 can be a recessed area on the surface of the housing bottom 102, having a lip running along the top of the recessed area and at least one end of the recessed area can be flush with the surface of the housing bottom 102. This end of the recessed area that is flush with the surface of the housing bottom 102 can be receive a standard tongue depressor that is held in place by the lip running along the top of the recessed area.

Figure 5:
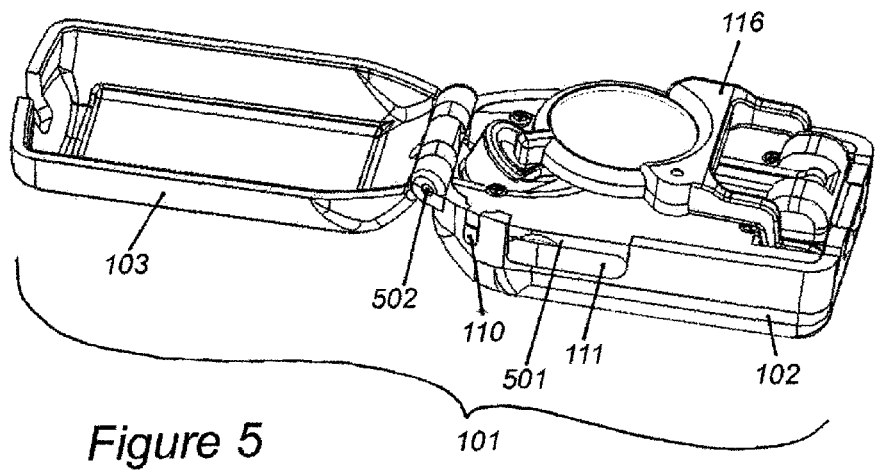
FIG. 5 is a view of a portable diagnostic instrument with the cover in the open position and its magnifying lens assembly and specula assembly folded inside of the bottom housing according to an embodiment.

FIG. 5 is a view of a portable diagnostic instrument 101 with the cover 103 in the open position and its magnifying lens assembly 116 and specula assembly 117 folded inside of the bottom housing 102 according to an embodiment.

A charging port 501 is visible in FIG. 5, which shows all of the components of the device 101 at their respective closed positions within the housing bottom 102 and the housing cover 103 is shown its open position. The charging port can be covered by a gasket 111 that can protect the port from environmental conditions. Located between the housing hinge 502 and the charging port 501 can be a clear plastic light pipe 110, with a light emitting diode (not shown) of more than one color located to the inside of the light pipe 110. The light emitting diode can indicate the charging status of the device 101 when it is connected to a power source. The diode can be one color when fully charged, another when charging and can flash a third color when the battery will not accept a charge.

Figure 6:
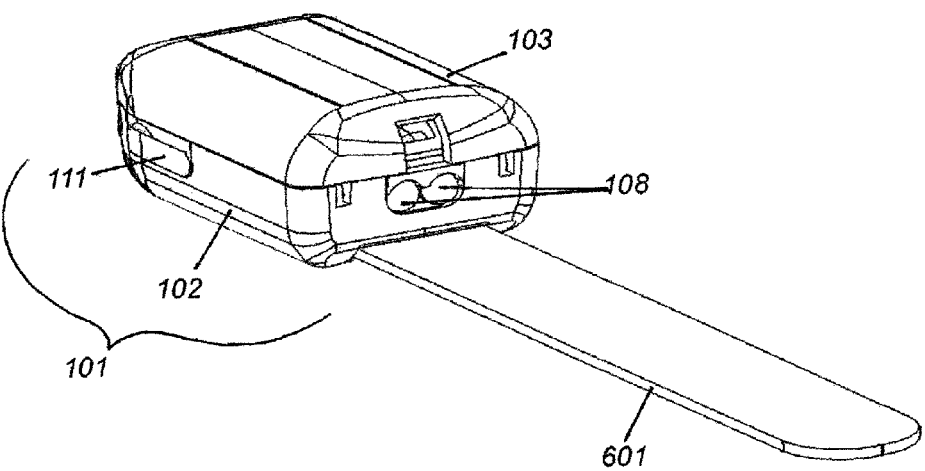
FIG. 6 is view of a portable diagnostic instrument in the fully closed position with a tongue depressor removably connected to a slot in the housing bottom according to an embodiment.

FIG. 6 is view of a portable diagnostic instrument 101 in the fully closed position with a tongue depressor 601 removably connected to a slot in the housing bottom 102 according to an embodiment.

A second embodiment that indicates another use of the diagnostic device 101 is demonstrated in FIG. 6. The housing cover 103 is in the closed position with the housing bottom 102. A tongue depressor 601 is inserted into a slot located on the outside of the housing bottom 102 and sized to receive a standard-sized tongue depressor. Two light emitting diodes 108 are located in an opening 107 in the housing bottom 103. These diodes 108 provide illumination of the specimen during use of the tongue depressor 601 and the diodes' 108 light intensity can be controlled by the circuit board 113 within the portable diagnostic instrument 101. The circuit board 113 can control the amount of power that is received by the diodes 108 thereby maintaining the light output at a constant level even when the battery potential decreases.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A portable diagnostic instrument comprising:
a case comprising:
a specula assembly adapted to fold and unfold from the case and a magnifying lens assembly adapted to fold and unfold from the case independently from the folding and unfolding of the specula assembly and comprising a light source, the specula assembly and the magnifying lens configured to operate together as an otoscope;
a sensor measuring an amount of electricity provided to the light source by a battery and a processor increasing current from the battery to the light source in order to provide constant light output until the battery no longer provides sufficient current to maintain the constant output; and
a warning unit to determine when the battery is about to fail and upon failure to notify a user of the portable diagnostic instrument.

2. The portable diagnostic instrument as described in claim 1 wherein the case operates as a handle when the portable diagnostic instrument is used as an otoscope.

3. The portable diagnostic device as described in claim 1 wherein the magnifying lens assembly comprises a support piece which is connected to the case and is also connected to a hinged lens capable of moving laterally form the support piece providing access to the specula assembly and the patient.

4. The portable diagnostic device as described in claim 1 wherein the specula assembly and the magnifying lens assembly are moveably connected to the case by a hinge.

5. The portable diagnostic instrument as described in claim 1 wherein the light source comprising the specula assembly further comprises one or more photodiodes and a light pipe capable of allowing light from the photodiodes to be transmitted through the light pipe to the patient.

6. The portable diagnostic instrument as described in claim 5 wherein the light pipe is conical in shape.

7. The portable diagnostic instrument as described in claim 5 wherein the specula assembly comprises a flexible printed circuit board, which transmits and controls electricity supplied to the surface mount photodiodes.

8. The portable diagnostic instrument as described in claim 5 wherein a conical photodiode is used in place of the photodiodes and light pipe combination.

9. The portable diagnostic instrument as described in claim 1 wherein the specula apparatus comprises a specula housing that is capable of receiving a disposable specula cover.

10. The portable diagnostic instrument as described in claim 1 wherein the case comprises a slot for removably connecting a standard tongue depressor to the portable diagnostic instrument.

11. The portable diagnostic instrument as described in claim 9 wherein photodiodes are located in an opening in the case allowing the user to illuminate the inside of a patient's mouth while using a tongue depressor removably connected to the slot comprising the case.

12. The portable diagnostic instrument as described in claim 1 wherein a housing bottom comprising the case further comprises an opening containing a blue film which is used to observe damage to an eye, which is visible after the introduction of fluorescein dye into the eye.

13. The portable diagnostic instrument as described in claim 1 wherein the battery is rechargeable.

14. The portable diagnostic instrument as described in claim 1 wherein the warning unit comprises a diode which is one color when fully charged and another when a charge is needed soon and flashes when the device should not be used and needs to be recharged.

* * * * *